United States Patent [19]
Barry et al.

[11] Patent Number: 5,143,849
[45] Date of Patent: Sep. 1, 1992

[54] TIP TO SURFACE SPACING FOR OPTIMUM DISPENSING CONTROLLED BY A DETECTED PRESSURE CHANGE IN THE TIP

[75] Inventors: James V. Barry, Rochester; Raymond F. Jakubowicz, Rush; J. Eric Hamann, Spencerport, all of N.Y.

[73] Assignee: Eastman Kodak Company, Rochester, N.Y.

[21] Appl. No.: 672,980

[22] Filed: Mar. 21, 1991

[51] Int. Cl.⁵ ............... G01N 35/02; G01N 35/08; B01L 3/02
[52] U.S. Cl. .................................. 436/50; 436/54; 436/180; 422/63; 422/67; 422/100; 73/863.01; 73/864.24
[58] Field of Search ............... 436/50, 54, 180; 422/100, 63, 67; 73/863.01, 864.23, 864.24, 864.25; 141/1, 193, 250, 291, 263; 222/160

[56] References Cited

U.S. PATENT DOCUMENTS

| | | |
|---|---|---|
| 4,340,390 | 7/1982 | Collins et al. . |
| 4,347,875 | 9/1982 | Columbus . |
| 4,586,546 | 5/1986 | Mezei et al. .................... 422/100 |
| 4,615,360 | 10/1986 | Jacobs . |
| 4,675,301 | 6/1987 | Charneski et al. . |
| 4,737,344 | 4/1988 | Koizumi et al. ................ 422/100 |
| 4,794,085 | 12/1988 | Jessop et al. . |
| 5,059,393 | 10/1991 | Quenin et al. ................. 422/100 |

Primary Examiner—James C. Housel
Assistant Examiner—Jan M. Ludlow
Attorney, Agent, or Firm—Dana M. Schmidt

[57] ABSTRACT

A method for automatically adjusting a dispensing tip from a surface onto which liquid is to be dispensed, a proper distance that precludes the dispensing stream from puddling up, or from breaking apart. The method features the formation on the tip of a meniscus of a nominal small volume and advancing the tip and meniscus until the surface is contacted. The resulting decrease in pressure in the tip is measured, to trigger the tip to stop its advance and to start dispensing. In circumstances wherein the contacted surface is hydrophobic so as to ideally require a meniscus depth greater than the nominal depth, the tip is retreated from the surface, during dispensing, to the ideal depth.

7 Claims, 6 Drawing Sheets

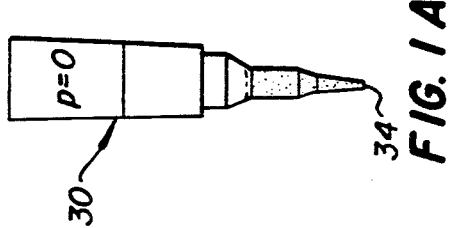
FIG. IA
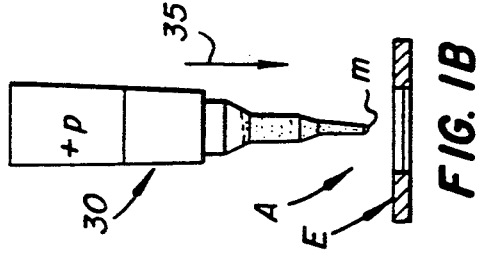
FIG. IB
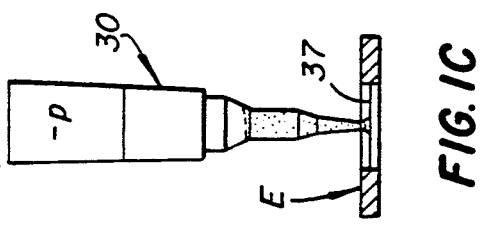
FIG. IC
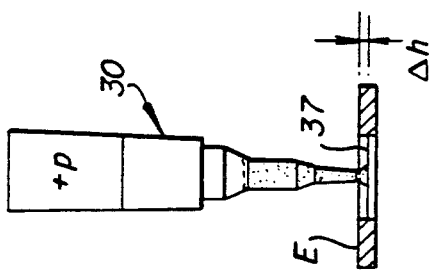
FIG. ID
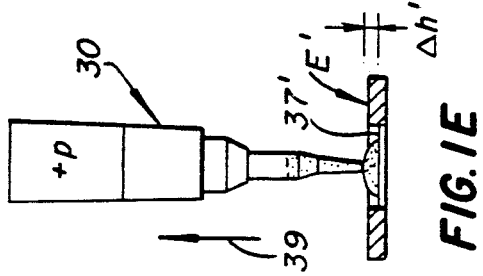
FIG. IE
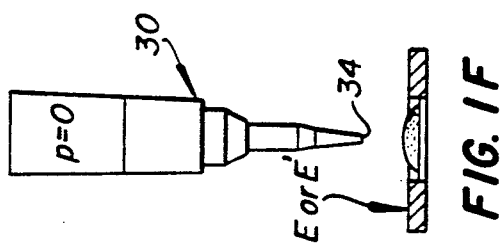
FIG. IF
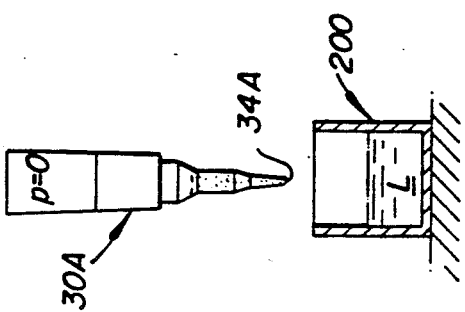
FIG. 10A
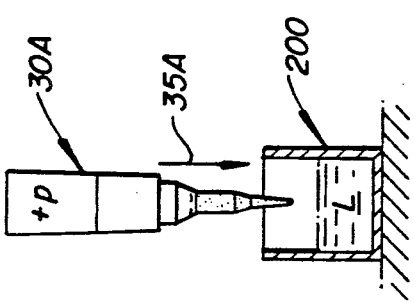
FIG. 10B
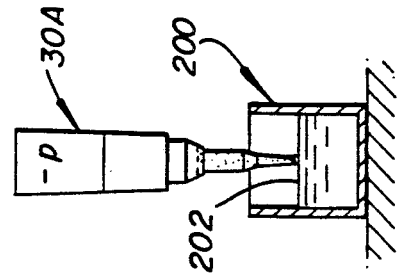
FIG. 10C
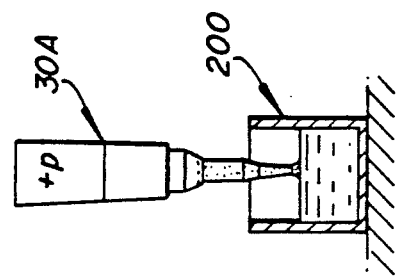
FIG. 10D

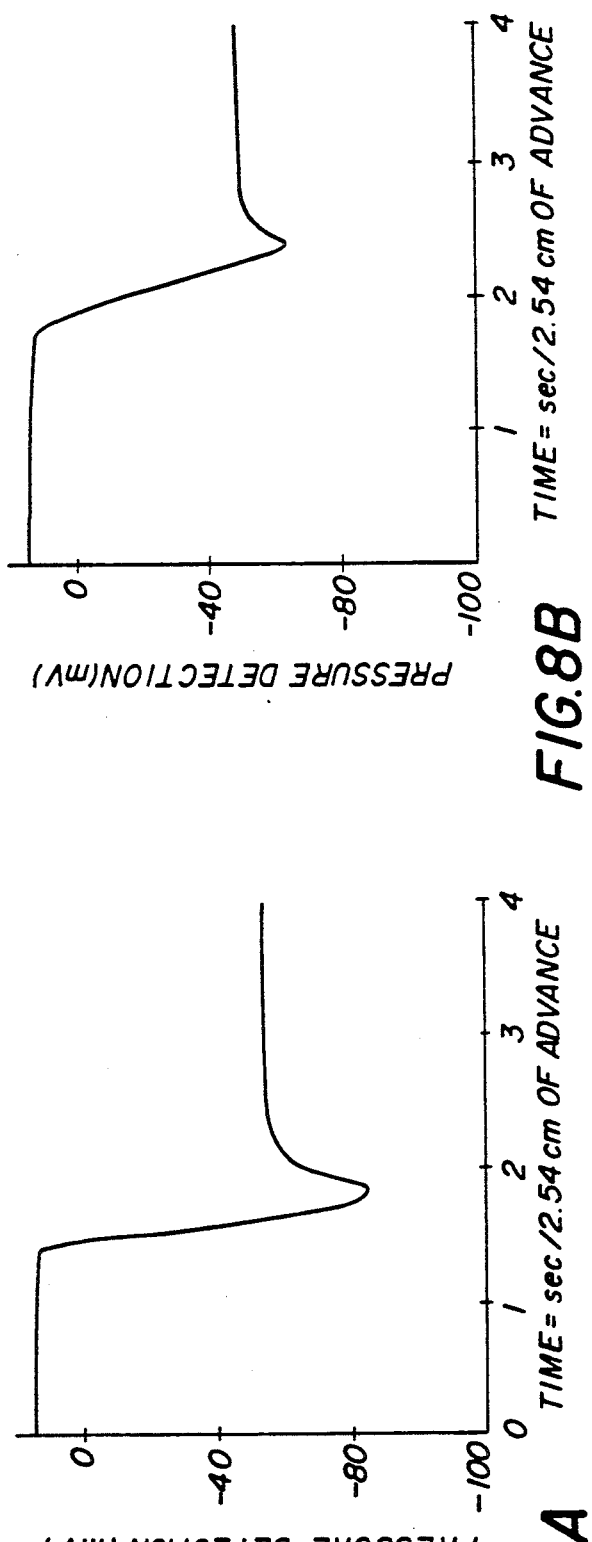
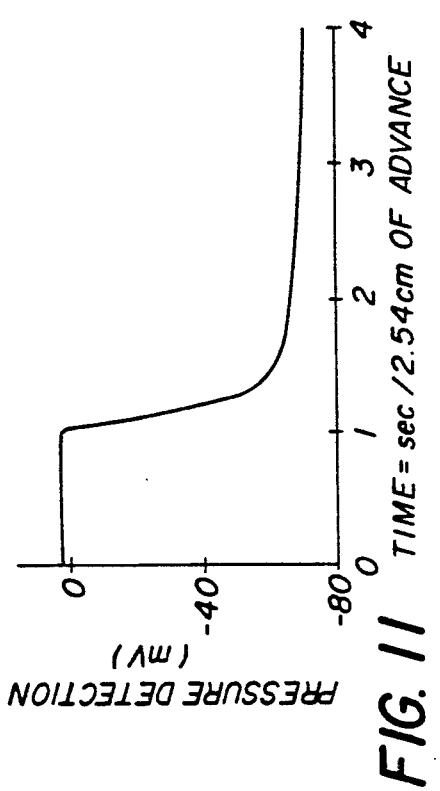
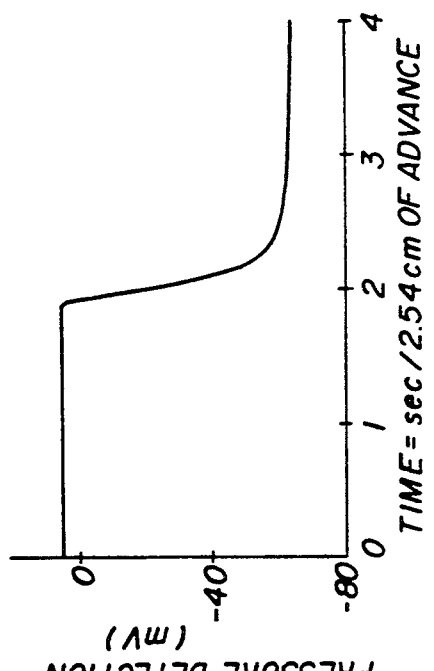

TIP TO SURFACE SPACING FOR OPTIMUM DISPENSING CONTROLLED BY A DETECTED PRESSURE CHANGE IN THE TIP

FIELD OF THE INVENTION

The invention is directed to a method of dispensing liquid onto a solid or a liquid surface, and especially, a method for automatically achieving optimal spacing for such dispensing by the use of pressure feedback.

BACKGROUND OF THE INVENTION

The last decade of developments in the field of clinical analyzers has seen a trend away from wet assays using liquid reagents, to dried ones using slide test elements. The purpose, of course, is to eliminate liquids and their attendant difficulties in handling. This need to avoid liquids has become even more important, as non-Earth environments became sites for such analyzers. For example, bulk liquids create a serious handling problem in the zero gravity environment of space.

The slide test elements available under the trademark "Ektachem" test elements, assayed on analyzers available under the trademark "Ektachem" analyzers, both from Eastman Kodak Company, have largely eliminated the noted liquid handling problems. There remains, however, even with such test elements the need to deposit a small quantity of patient sample liquid onto the test element. That quantity in turn must somehow be obtained from a larger patient sample reservoir. Aspirating probes with disposable tips have been used for this purpose. Because such tips have to be wetted on the outside to aspirate sample into the inside, this pre-wetting of the tips has led to the need for removal of exterior liquid that can otherwise cause perfusion. (Perfusion is the deflection of liquid dispensed from a probe tip, up the outside surface of the tip instead of onto a receiving slide test element).

A variety of techniques have been used to control the liquid on the exterior surface to prevent perfusion. One of the most common has been to configure the structure of the tip to discourage exterior liquid from remaining in position to affect the dispensing operation. Examples are described in U.S. Pat. No. 4,347,875. Such tips can be further provided with a wax coating to discharge retention of exterior liquid, also as described in said '875 patent, column 5. Yet another technique is to "cut", i.e., blow, the exterior liquid away with an air knife, as described in U.S. Pat. No. 4,615,360. Still another technique is to absorptively wipe off the tip each time liquid is aspirated or dispensed, but wiping creates serious problems in automated apparatus and biohazards.

With the exception of the wiping technique, each of the aforementioned solutions has met with considerable success. Nevertheless, another source of perfusion remains. That is, the aspirating probe is intended to dispense the small quantity of patient sample as a steady stream, onto an object or surface such as a dried test element. The stream must not proceed too fast, lest it puddle on the surface and encourage perfusion by wetting the tip exterior. It must not proceed too slowly, lest the stream break apart into droplets that can spatter upon impact, and provide unexpected distribution on the test element that forms ringing. Unfortunately, the rate of acceptance of the stream into the test element, which of course is the controlling factor governing this problem, depends on some variables: the wettability of the surface of the slide test element, the fluid characteristics of the patient sample, and the tip-to-element spacing.

Of these variables, the variation in wettability of the test element is a predictable function of the chemistry of that element. That in turn is dictated by the assay to be run, a factor that the analyzer can keep track of. Presumably, if this were the only controlling variable, the analyzer could be reset with a certain tip-to-element spacing, each time a new chemistry is presented to the probe. This, however, presumes that close manufacturing tolerances have been used, so that the desired reset spacing will in fact be achieved each time. Because such close tolerances are a major cost burden, resetting the spacing to a fixed value is not considered an adequate solution. In addition, even if cost were not a factor, such fixed resetting will not accommodate the problem created by patient sample variations. That is, the liquid surface tension of the samples is normally not known in advance and hence is not a datum that is entered with the patient I.D. Great variations in surface tension occur in, e.g., blood serum, primarily due to the existence of the very diseased states that are sought to be detected.

Yet another problem with conventional analyzers has been that the slide test element on which the sample liquid is to be dispensed, can be bowed out of its nominally planar configuration. This in turn will adversely affect the tip-to-element spacing that needs to be controlled to provide optimum stream flow. Such bowing is also difficult to detect or predict in advance.

Therefore, there has been a great need prior to this invention to provide a dispensing station for an analyzer that can automatically adjust the tip-to-element spacing regardless of which of the above-noted factors has changed in an unpredictable way.

Pressure transducers have been used with dispensing probes in prior analyzers. For example, in U.S. Pat. No. 4,340,390, a pressure transducer is described to sense, among others, things such as plugged probes, and the complete separation of the fluid or liquid that is in the probe, from the test element, column 7, lines 18–20. This sensing technique, in which the pressure registers as "zero" due to the complete break, is also used in the '390 invention to indicate completion of the dispensing step.

Still other uses have been made of such transducers, as described, for example, in U.S. Pat. No. 4,675,301. That is, inadvertent pressure changes within the probe are monitored so that the liquid meniscus always starts from about the same position for the dispensing step. Such a procedure however does not address the problems of spacing between probe and test element discussed above. Instead, it assumes that pre-set spacings will be satisfactory. As described above, this is not always the case.

Finally, a recent use of pressure transducers is described in U.S. Pat. No. 4,794,085. Such a system causes the dispenser to pressurize (or draw a vacuum on) the air in the tip at a certain height to sense if the empty tip has yet contacted liquid to be aspirated. Once contact is achieved, the pressure reading will change. Such a system is not satisfactory to handle the intercept of a full tip's liquid, with either a liquid or a solid, since a full tip cannot readily alter the interior pressure to sense the exterior conditions.

Thus, the conventional use of pressure transducers has not solved the need for automatic adjustment of tip-to-element spacing described above.

SUMMARY OF THE INVENTION

We have devised a method for automatically ascertaining the location of the surface on which the liquid is to be dispensed, and for maintaining the proper distance from that surface during dispensing, as a solution to the aforesaid problems.

More specifically, in accord with one aspect of the invention, there is provided a method for dispensing a variety of different body liquids in a controlled stream onto a plurality of different test elements, using dispensing means for dispensing a body liquid and comprising a dispensing tip, transducer means for detecting the pressure applied to a body liquid in the dispensing means and means for altering the pressure, and means for moving the dispensing means relative to a test element. The method comprises the steps of a) aspirating a body liquid of unknown surface tension into the dispensing tip, b) advancing the tip with liquid in it towards a supplied test element, c) during step b), creating an exterior meniscus of liquid from the tip with the altering means and detecting any pressure changes in the tip with the transducer means, d) automatically sensing the intercept of the meniscus with the supplied test elements by detecting with the transducer means a predetermined amount of decrease in pressure, e) terminating the advancing of the step b) upon sensing the decreased pressure in step d) to create a tip-to-element spacing, and f) dispensing with the altering means, liquid from the tip, so that proper tip-to-test element spacing is achieved during step f) regardless of poor mechanical tolerances.

In accord with another aspect of the invention, there is provided a method for dispensing a variety of different body liquids in a controlled stream onto a second liquid surface using dispensing means for dispensing a body liquid and comprising a dispensing tip, transducer means for detecting the pressure applied to a body liquid in the dispensing means and means for altering said pressure, and means for moving the dispensing means relative to a container of the second liquid. The method comprises the steps of a) aspirating a body liquid of unknown surface tension into the dispensing tip, b) advancing the tip with liquid in it towards a supplied container of a second liquid, c) during step b), creating an exterior meniscus of liquid from the tip with the altering means and detecting the pressure changes in the tip with the transducer means, d) automatically sensing the intercept of the meniscus with the second liquid by detecting with the transducer means a predetermined amount of decrease in pressure, e) terminating the advancing of the step b) upon sensing the decreased pressure in step d) to create a tip-to-element spacing, and f) dispensing with the altering means, liquid from the tip, so that proper tip-to-liquid spacing is achieved during step f) regardless of variable fluid levels.

Accordingly, it is an advantageous feature of the invention that the dispensing tip automatically seeks out and maintains the proper height distance from the surface onto which liquid is to be dispensed.

It is a related advantageous feature of the invention that the method of dispensing provided by the invention avoids the extremes of dispensing too fast so that puddling and perfusion occur, and dispensing too slowly so that the stream breaks up and creates problems.

It is a further advantageous feature of the invention that the dispensing method can alter the dispense height used for intercept detection to accommodate greater heights required to avoid puddling, without altering the expected pressure profile.

Other advantageous features will become apparent upon reference to the following Description of the Preferred Embodiments, when read in light of the attached drawings.

BRIEF DESCRIPTION OF THE DRAWINGS

FIGS. 1A–1F are partially schematic elevational views illustrating the practice of the invention when applying patient sample to a dried slide test element;

FIGS. 7A–7B, 8A–8B and 9 are representative pressure profile plots of liquid dispensed onto representative test elements, in accord with the invention;

FIG. 10A–10D are schematic illustrations similar to those of FIGS. 1A–1G, but illustrating an alternate embodiment of the invention; and FIG. 11 is a pressure profile similar to that of FIG. 7A, but for the embodiment of FIG. 10C.

DESCRIPTION OF THE PREFERRED EMBODIMENTS

The invention is hereinafter described in the context of the preferred embodiments, wherein certain preferred dispensing tips are used in a preferred analyzer to dispense liquid, most preferably, blood serum, onto preferred surfaces such as test elements that are dried, slide elements such as the type manufactured under the tradename "Ektachem" by Eastman Kodak Company, or "Drychem" by Fuji. In addition, the invention is useful regardless of the liquid being dispensed, the kind of dispensing tip or analyzer that is used, and regardless of whether the surface is a dried slide test element, or even any kind of test element, since the method can also be used to detect the dispense height above a liquid surface.

Figure 2:
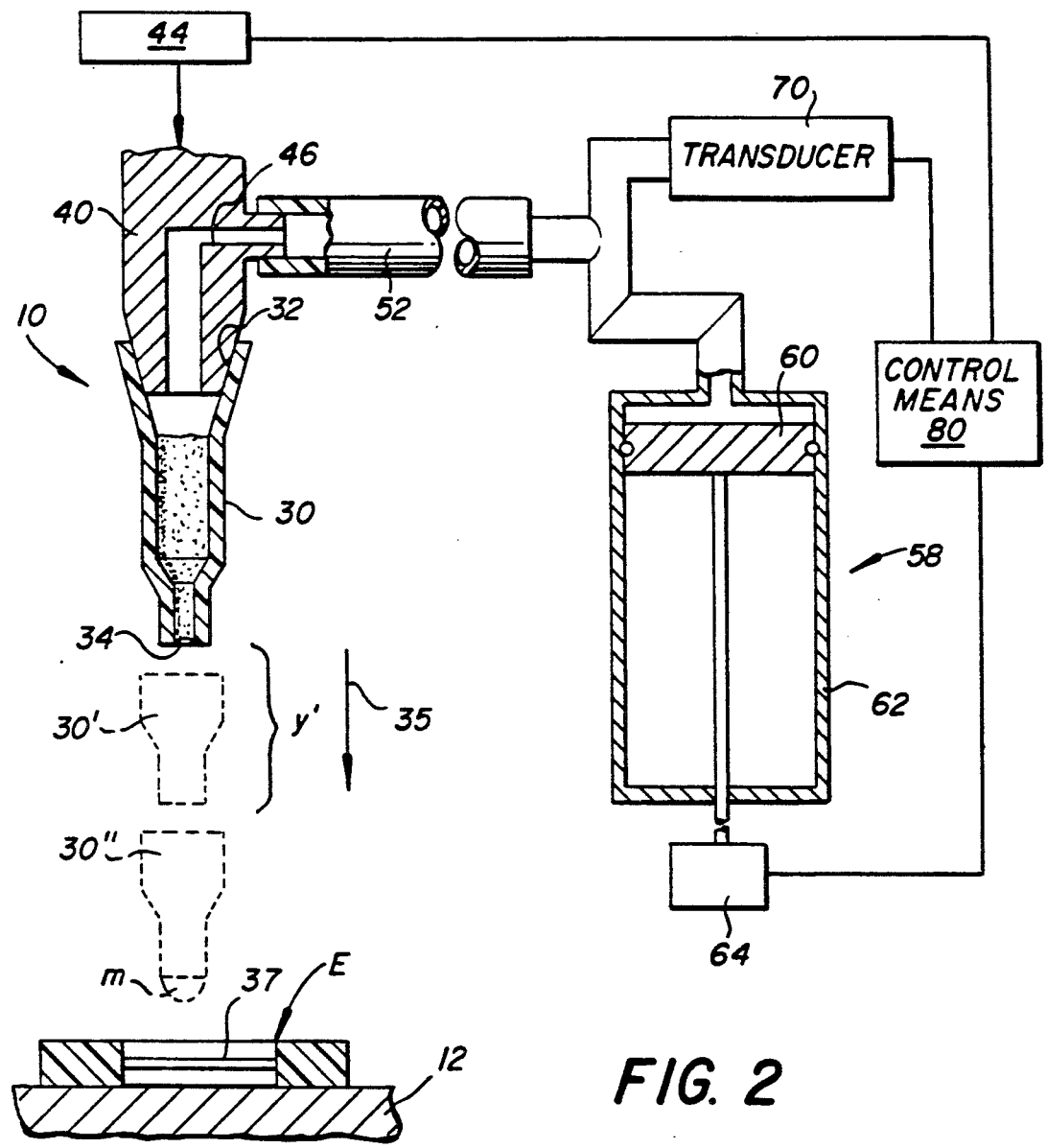
FIG. 2 is a partially schematic fragmentary elevational view of apparatus useful in the invention.

The method of the invention is best understood from FIGS. 1A–1F, using apparatus such as the apparatus shown in FIG. 2. That is, a dispenser (not shown in FIGS. 1A–1F) has a disposable tip 30 mounted thereon with a dispense aperture 34, the tip being of any convenient type. (The tips available under the tradename "DT-60" tips from Eastman Kodak Company are shown). At a suitable aspirating station, such a tip is filled with an appropriate volume of patient sample, e.g., 10 μL of blood serum, and following aspiration, the pressure inside tip 30 is essentially equal to zero (FIG. 1A). Next, a slide test element E is positioned under tip 30 at a dispense station A, FIG. 1B. At this station and time, two events occur—the pressure in tip 30 is momentarily increased to a +p value sufficient to form a small meniscus "m" of predetermined volume at aperture 34, and, the tip is slowly advanced, arrow 35, towards element E. After meniscus "m" is formed, the pressure inside tip 30 returns to a slightly positive value, since a full drop is not formed. That pressure remains constant, until the meniscus intercepts surface 37 of test element E, FIG. 1C. At that time, the liquid of the meniscus wicks off onto the test element, and if the volume of the meniscus is the proper amount, the pressure inside tip 30 becomes significantly negative, as shown by "−p". When this negative change in pressure is detected, the downward movement of tip 30 is ceased, and the spacing is established at the nominal value for this predetermined volume.

It will be readily appreciated that this method of detecting the location of surface 37 is totally independent of where surface 37 ends up actually being. That is, surface 37 can be displaced a considerable vertical distance beyond the expected location, and still tip 30 will set itself at the optimum spacing, provided, of course, that the unexpected displacement still locates it below the location of aperture 34 prior to meniscus formation, FIG. 1B.

Next, the pressure inside tip 30 is increased an appropriate amount (+p) by the apparatus of FIG. 2, to initiate the dispensing of the liquid, FIG. 1D, at an appropriate dispense rate. At this time, the spacing between surface 37 and tip aperture 34 is the nominal value of Δh, the details of which are illustrated hereinafter.

In some cases, it will be necessary to gradually increase the spacing Δh during dispensing, to a value of Δh', FIG. 1E. The reason is that some surfaces, including some test elements E', are so hydrophobic that the liquid when it is dispensed, does not get absorbed. Instead, it tends to build up on surface 37, which, in turn, increases the chances of the liquid perfusing up tip 30. To avoid this, tip 30 is withdrawn, arrow 39, at a rate consistent with the build-up of the liquid on surface 37, to the larger value Δh'. (This build-up rate and rate of withdrawal varies, depending on how hydrophobic a particular chemistry is in element E'). This greater distance Δh' is not used as the value for the preformed meniscus "m", since in some cases, e.g., for a 2 μL volume, this can be so large as to itself be a threat to perfusion should it be formed as a pendant drop from the downwardly-moving tip.

Eventually, the dispensing is completed, FIG. 1F, and only at this time does the flow stream cease at aperture 34. The pressure inside the tip returns to its nominal zero value. As shown in FIG. 1, tip 30 in question dispensed its entire contents onto a single test element, due to the volume of the tip. Larger tips, however, will dispense only a fraction of the total liquid initially present, by the time the stage of FIG. 1F is reached.

Suitable analyzer apparatus 10 for carrying out the steps of FIGS. 1A-1F are shown in FIG. 2. Such an analyzer uses conventional parts, heretofore known as shown for example in U.S. Pat. No. 4,794,085. That is, a tip 30 is removably mounted at its larger aperture 32 onto an aspirator/dispenser probe 40. Probe 40 is moved relative to a test element E suitably supported at 42. That is, probe 40 is moved preferably up and down, by a conventional drive 44. Probe 40 has an internal passageway 46 connected to a pressure transducer 70 via a hose 52, and also to means 58 for altering the pressure inside tip 30. Such means 58 comprise a piston 60 moved inside a cylinder 62 by a drive means 64, between the various positions shown in phantom. Control means 80 is used to detect the pressure signal generated by transducer 70, and in turn acts upon both drive means 44 and 64 in accordance with an appropriate program to control the movement and pressure, respectively, of tip 30. Control means 80 is preferably a microcomputer in analyzer 10, and transducer 70 is one having a high sensitivity, low internal air volume and high stability, for example, a Motorola MPX Series Piezo-Resistive Pressure Sensor or strain gauge transducer.

Movement of tip 30, arrow 35, is in increments, so that aperture 34 moves first a distance Y' to the phantom position 30', and then to phantom position 30", and so forth, until the meniscus m, formed as movement occurs, intercepts surface 37.

Any suitable tip locator, not shown, can be used to stabilize and orient tip 30 relative to element E. For example, a twin tip locator of the type shown in U.S. Pat. No. 4,797,257 is useful, regardless of the kind of analyzer otherwise being used. However, the tip locator is modified to allow freedom of movement of tip 30 along the vertical axis, to achieve whatever Δh spacing is called for by the chemistry of element E.

Figure 3:
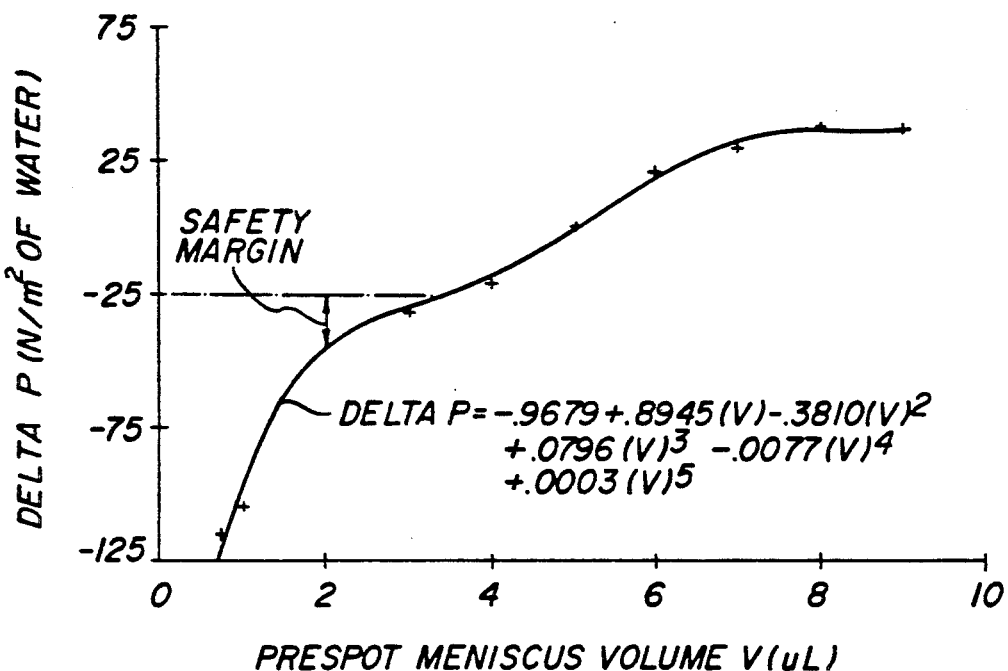
FIG. 3 is a pressure profile of the change in pressure that occurs at FIG. 1C, as the volume of the meniscus is varied.

It is a surprising discovery of the invention that only certain sizes of meniscii "m" will produce a decrease in pressure, −p, FIG. 1C, upon contact with a wicking surface, that is, upon contacting any dried slide test element or the surface of liquids of choice. Above a certain value, the pressure inside the tip, at the time of intercept, either does not change, or actually is increased, due to the momentum of the large meniscus volume that has ceased movement due to the contact. The actual meniscus volume amount that is needed to produce this phenomenon will vary, depending upon the tip geometry or velocity and the hydrophobicity between the contacting surface and fluid. FIG. 3 illustrates a typical example, using a "DT-60" tip (noted above) and an "Ektachem" glucose test element (also noted above). The liquid dispensed was water, but it is believed to be typical of most aqueous liquids for this tip and this test element. Thus, when the volume of meniscus "m", FIG. 1B or FIG. 2, reached 5 μL, the pressure change detected in tip 30 upon contact with test element E was zero, and the pressure change became positive for volumes larger than 5 μL. Therefore, the maximum volume of "m" that is useful, to avoid an ambiguity in the reading of the pressure change, is 4 μL. Preferably, only 3 μL or smaller meniscii are used, to account for slight differences due to wettability changes in the test element, etc. Furthermore, volumes between 3 μL and 4 μL suffer the disadvantage of requiring a more sensitive threshold, that is, a threshold detection of less than −25 N/m² of water.

Because there is needed a margin of safety, that is, a dip in the pressure that reliably indicates touch-off of the liquid free from any noise in the system, most preferably the volume that is pre-formed on the tip is 2 μl or smaller. This allows a threshold pressure to be set at a Δp of −0.1 inch (25 N/m²) of water, and still produce a "safety margin", FIG. 3. For example, a volume of only 0.7 μL will produce a Δp signal of almost −125 N/m² of water, which is clearly in excess of −25 N/m² and thus clearly the touch-off event.

Thus, the preferred method of the invention is to use a pendant meniscus having a volume of 2 μl or less and to detect a decrease in pressure of at least 25.0 Newtons/m² (0.1 inches) of water (using 25 Newtons/m² as the threshold value to be exceeded as the intercept event.)

Figure 4:
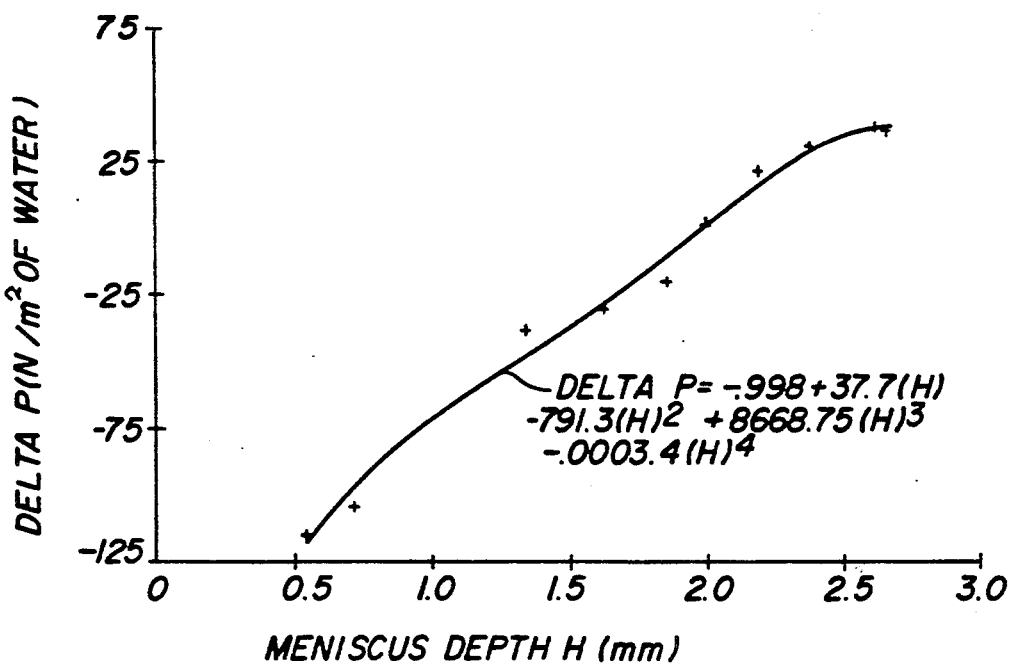
FIG. 4 is a pressure profile similar to that of FIG. 3, except the pressure change is plotted against the corresponding height of the varying meniscus.
Figure 5:
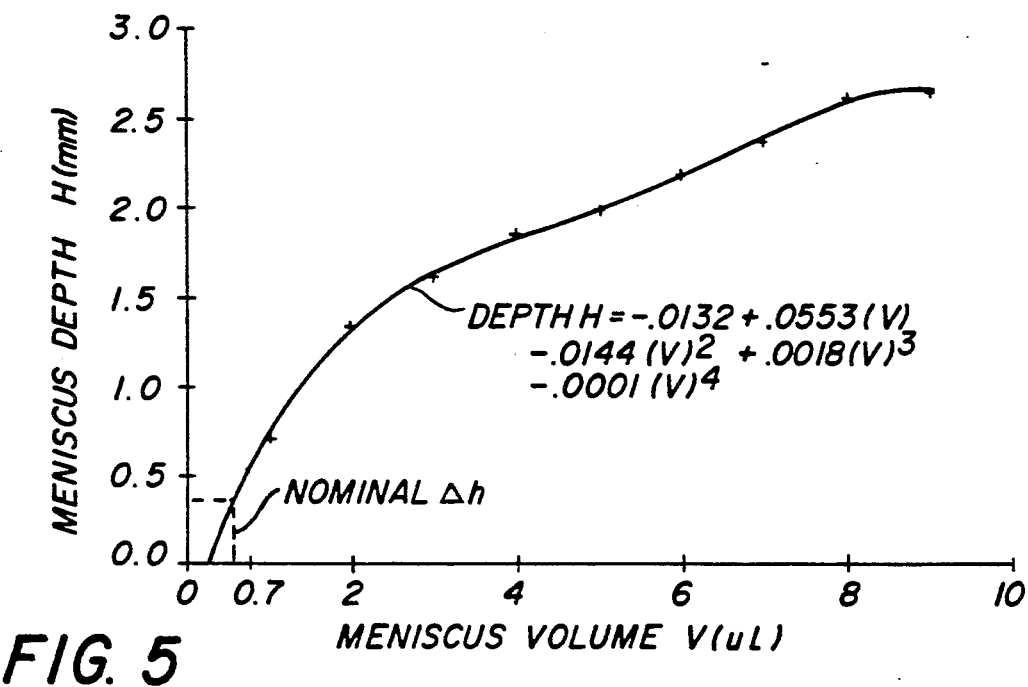
FIG. 5 is a plot of meniscus volume to meniscus height, by which the transformation of FIG. 3 to FIG. 4 is achieved.

FIGS. 4 and 5 are graphs that convert the relationship of FIG. 3 to either a plot of the meniscus depth H versus the change in pressure upon intercept, or the meniscus depth H versus its volume, respectively, for the same conditions as were tested for FIG. 3. As noted, the preferred or nominal meniscus depth is 0.3 mm.

The speed of dispensing of the liquid also will depend on the ability of the surface that is contacted to absorb the liquid. For body liquids dispensed onto test elements of the type described, a useful rate of dispensing, once the interception event is detected, is about 100 μl/sec.

Figure 6:
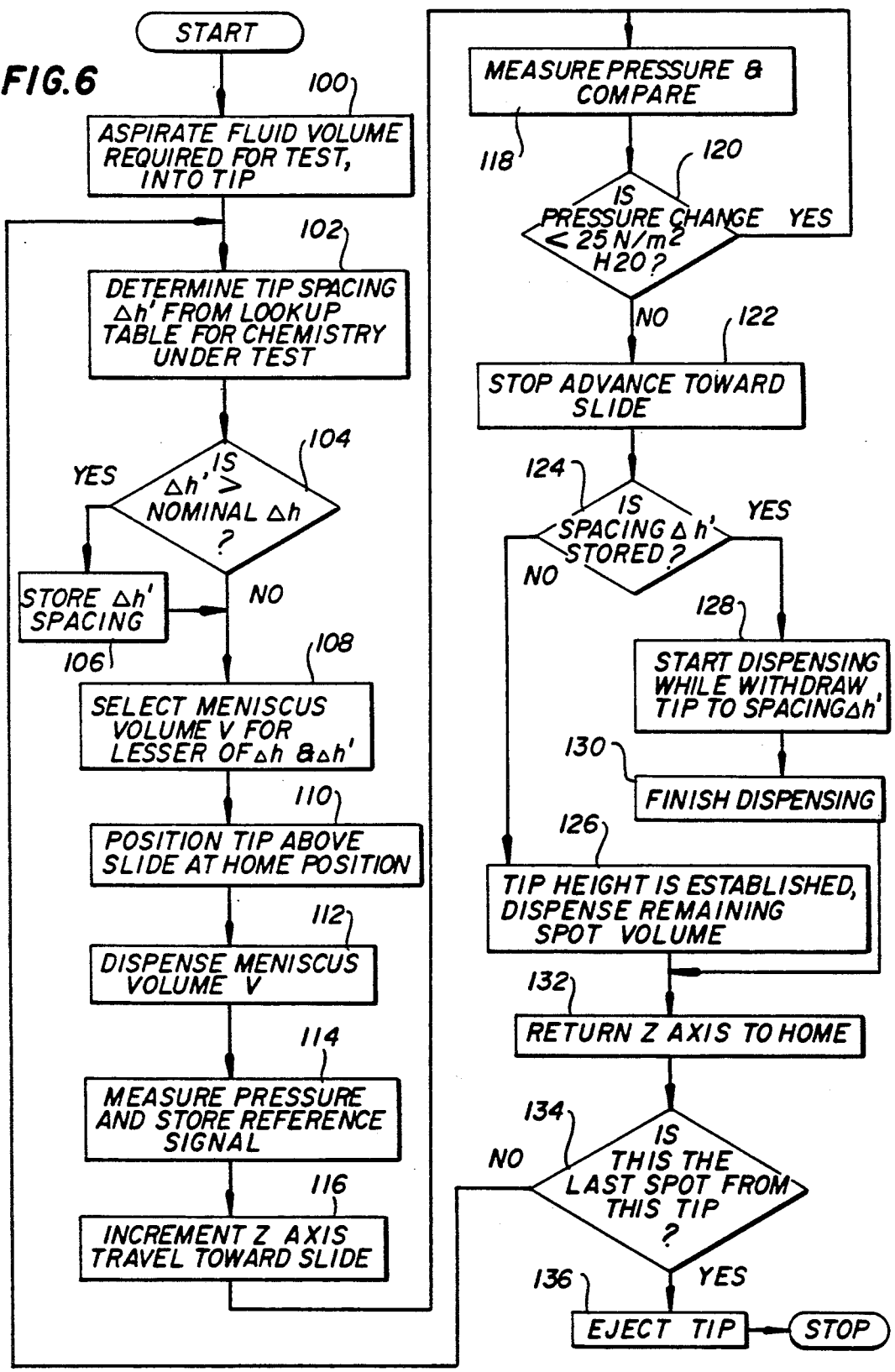
FIG. 6 is a flow chart illustrating the steps that are followed in programming an analyzer to carry out the method of the invention.

Any suitable program can be used in a conventional manner to program control means 80. The flow chart of FIG. 6 is illustrative of the steps of the computing process involved. The process requires, first, that sample be aspirated into tip 30, step 100. Next, since control means 80 already knows what sequence of assays is being run (from a bar code scan or from operator keying), a look-up table is checked, step 102, to determine the appropriate tip spacing, Δh', FIG. 1D, for that assay. This may or may not be the nominal tip height to be used, namely Δh.

Next, step 104, is Δh' greater than the nominal height Δh (the height shown in FIG. 1D)? If yes, that greater value is stored, step 106. If no, the program continues to the step, 108, of determining the meniscus volume for the lesser of the two Δh and Δh', from a look-up table, based for example on the plot of FIG. 5, where the lesser of Δh and Δh' is to correspond to the meniscus depth since that is what Δh or Δh' is, on contact. It will be appreciated that, although the nominal value for Δh is 0.3 mm±0.1 mm, there could be some chemistries where Δh' is less than this. In such a case, the meniscus volume "V" is selected to be this lesser value, rather than the nominal 0.7 μL.

Next, step 110, tip 30 is positioned at the home position, FIG. 1A, and meniscus volume V, selected in step 108, is dispensed, step 112. At this time, a pressure reference reading is made, step 114, and stored as the nominal "zero" value, against which future pressure changes are to be measured.

As tip 30 is incremented, step 116, along the vertical or Z axis towards an appropriate test element (as shown in FIG. 1B), the pressure inside tip 30 is continually measured, step 118, and compared against the "zero" reference value measured in step 114. As long as the pressure measured differs, step 120, from the zero value by less than 25 N/m² of H₂O, then the process is iterative and steps 116 and 118 are repeated. However, as soon as the pressure decreases from the reference value by >25 N/m² of H₂O, the program stops the tip advance, step 122, and, it exercises query 124 which checks for the ultimate tip spacing Δh' that will have been stored if it is greater than Δh. If the query is negative on such a stored value, no further movement of tip 30 is needed, and dispensing continues until completed, step 126.

However, in some chemistries, there will be stored a Δh' that is greater than Δh, and step 128 is then followed. For example, Δh' can be 0.7 mm. That is, the remaining liquid is dispensed while tip 30 is simultaneously withdrawn, eventually to that value Δh' (FIG. 1E). This precludes the liquid from puddling up on a hydrophobic surface 37' or disturbing the spreading layer during fluid dispensing. The liquid is then all dispensed for that element, step 130, FIG. 6, and tip 30 is returned to its home position, step 132, corresponding to that shown in FIG. 1A.

Next, the program queries whether no more volumes are to be dispensed, step 134, and if none are additionally needed, tip 30 is ejected, step 136. However, if more are needed, particularly for those tips whose initial volume of sample liquid is >10 μL, then the entire process is reiterated.

Figure 7A:
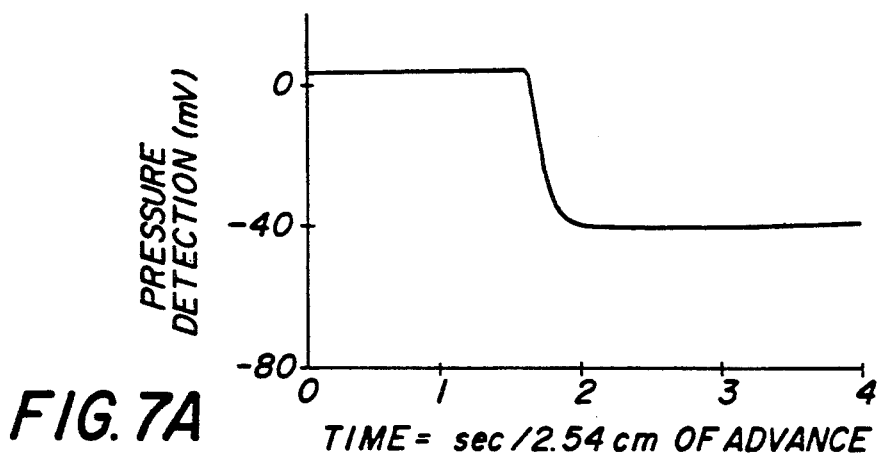
Figure 7B:
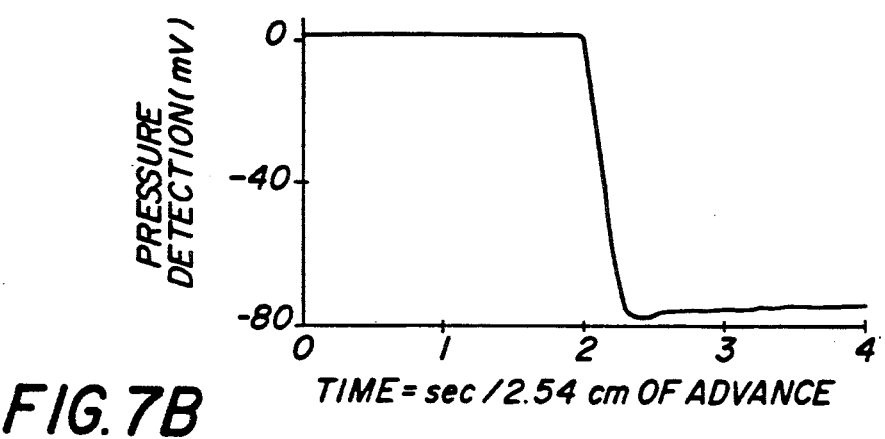

FIGS. 7A–7B illustrate typical pressure profiles measured for the touch-off event only, a relatively hydrophilic surface 37, FIG. 7A, or a relatively hydrophobic surface 37, FIG. 7B. In each case, the liquid dispensed was water using a 1 μL meniscus volume, and the test elements were, respectively, an "Ektachem" glucose slide and an "Ektachem" total protein slide. In the glucose case, FIG. 7A, the pressure decrease was indicated by an electrical signal that was slightly more than 40 mV. The threshold value corresponding to 25 N/m² of water was 30 mV. In this case, Δh' was in fact 0.3 mm, and the step of FIG. 1E would not have to be used (query 124 of FIG. 6 would answer in the negative). In the total protein case, the pressure decrease was almost 80 mV. During the dispensing steps 126–130, for this chemistry, a Δh' is in fact stored, steps 106 and 124, that is, Δh' is 0.7 mm and is >Δh. Thus, the tip spacing for total protein will increase during dispensing to about 0.7 mm.

FIGS. 8A–8B illustrate a similar effect, when synthetic liquid available from Eastman Kodak Company under the tradename "Koda-Control II", comprising bovine serum, was applied to the test elements used in FIGS. 7A and 7B, respectively.

A pressure profile similar to that of FIG. 8B (not shown) occurs when water is in a tip that touches off onto a pre-wetted test element, e.g., one pre-wetted with a liquid such as "Koda-Control II".

The process is also useful to detect the intercept of the dispensing tip with a non-absorbing surface, e.g., a glass slide. The results are indicated in FIG. 9, wherein water was touched off exactly as in the test of FIGS. 7A and 7B, but onto a glass slide. Complete dispensing was skipped, however, since the non-absorbing surface would cause too much perfusion. In FIG. 9, the increase in the negative trend after time $t_3$ is an equilibrium effect only.

It is not necessary that a solid be the surface that intercepts the meniscus to trigger the decrease in pressure. A liquid surface can also be detected, FIGS. 10A–10D. Parts similar to those previously described bear the same reference numeral, to which the distinguishing suffix A is appended.

Thus, FIG. 10A, tip 30A already containing patient sample is in a home position, and in FIG. 10B, it starts to advance, arrow 35A, while a meniscus "m" is formed at aperture 34A by an increase in pressure (+p), as in the previous embodiments. However, it is advanced towards, not a test element, but rather any suitable container 200, holding any liquid L. For example, the liquid can be a diluting liquid whereby patient sample can be diluted. Such dilutions are conventionally done to retest a sample showing an out-of-range condition for a particular analyte. When meniscus "m" encounters surface 202 of liquid L, FIG. 10C, a pressure decrease (−p) is detected in tip 30A, more than a threshold value, and tip 30 ceases its advance. Instead, FIG. 10D, the pressure is increased in tip 30A (+p), and the liquid contents are injected into container 200. Depending upon the surface area of surface 202, tip 30A can be gradually withdrawn during this step to prevent undue wetting of the exterior of the tip.

Alternatively (not shown), the liquid in tip 30A can be the diluting liquid, e.g., water, and the liquid in container 200 can be the patient sample.

FIG. 11 is an illustration of the pressure profile for such a liquid-liquid embodiment, wherein the conditions are identical to those of the test of FIG. 7A, except that the water of the tip intercepted "Koda-Control II" liquid in a beaker.

Such a use of the invention for liquid-liquid intercepts is useful, because it is not always known where the surface 202 of the liquid, FIG. 10C, will be. Alternatively, it avoids the necessity for the liquid of container 200 to be added in precise volumes, or that surface 202 be otherwise detected, for example using an optical sensor.

The invention has been described in detail with particular reference to preferred embodiments thereof, but it will be understood that variations and modifications can be effected within the spirit and scope of the invention.

What is claimed is:

1. A method for dispensing a variety of different body liquids in a controlled stream onto a plurality of different test elements, using dispensing means for dispensing a body liquid and comprising a dispensing tip, transducer means for detecting the pressure applied to a body liquid in said dispensing means and pressure altering means for altering said pressure, and means for moving said dispensing means relative to a test element, the method comprising the steps of
   a) aspirating a body liquid of unknown surface tension into said dispensing tip,
   b) advancing said tip with liquid therein towards a supplied test element,
   c) during step b), creating an exterior meniscus of liquid protruding from said tip with said pressure altering means and detecting any pressure changes in said tip with said transducer means,
   d) automatically sensing the intercept of said meniscus with the test element by detecting with said transducer means a predetermined amount of decrease in pressure,
   e) terminating the advancing of step b) upon sensing said decrease in pressure in step d) to create a tip-to-element spacing, and
   f) dispensing liquid from said tip with said pressure altering means,
   so that proper tip-to-test element spacing is achieved during step f) regardless of poor mechanical tolerances.

2. A method as defined in claim 1, and further including the step of f') increasing said tip-to-element spacing during the dispensing by a selected amount, to an optimum spacing for a given test element.

3. A method as defined in claim 2, and further including the steps of
   a') storing the order and identity of test elements to be supplied to said dispensing means and
   g') altering said selected amount of increase in spacing, dependent upon the identity of the test element known to be present from said storing step a').

4. A method as defined in claim 1, and further including the steps of
   a') storing the order and identity of test elements to be supplied to said dispensing means and
   g') altering said tip-to-element spacing of step e), dependent upon the identity of the test element known to be present from said step a').

5. A method for dispensing a variety of different body liquids in a controlled stream onto a liquid surface using dispensing means for dispensing a body liquid and comprising a dispensing tip, transducer means for detecting the pressure applied to a body liquid in said dispensing means and pressure altering means for altering said pressure, and means for moving said dispensing means relative to a container of the second liquid, the method comprising the steps of
   a) aspirating a body liquid of unknown surface tension into said dispensing tip,
   b) advancing said tip with liquid therein towards a supplied container of a liquid surface,
   c) during step b), creating an exterior meniscus of liquid protruding from said tip with said pressure altering means and detecting any pressure changes in said tip with said transducer means,
   d) automatically sensing the intercept of said meniscus with the liquid surface by detecting with said transducer means a predetermined amount of decrease in pressure,
   e) terminating the advancing of step b) upon sensing said decrease in pressure in step d) to create a tip-to-liquid spacing, and
   f) dispensing liquid from said tip with said pressure altering means,
   so that proper tip-to-liquid spacing is achieved during step f) regardless of variable liquid levels.

6. A method of dispensing liquids as defined in claims 1 or 5, wherein step c) of creating an exterior meniscus produces a meniscus volume no greater than about 4 μL.

7. A method as defined in claim 6, wherein said decrease in pressure sensed in step d) exceeds 0.1" of water.

* * * * *